(12) United States Patent
Chen et al.

(10) Patent No.: US 10,994,081 B2
(45) Date of Patent: May 4, 2021

(54) AEROSOL GENERATING APPARATUS WITH REPLACEABLE PARTS

(71) Applicant: MICROBASE TECHNOLOGY CORP., Taoyuan (TW)

(72) Inventors: Yi-Tong Chen, Taoyuan (TW); Chih-Wei Lu, Taoyuan (TW); Ting-Kai Tsai, Taoyuan (TW); Po-Chuan Chen, Taoyuan (TW)

(73) Assignee: MicroBase Technology Corp., Taoyuan (TW)

( * ) Notice: Subject to any disclaimer, the term of this patent is extended or adjusted under 35 U.S.C. 154(b) by 0 days.

(21) Appl. No.: 16/098,136

(22) PCT Filed: Dec. 5, 2017

(86) PCT No.: PCT/CN2017/114632
§ 371 (c)(1),
(2) Date: Nov. 1, 2018

(87) PCT Pub. No.: WO2018/103636
PCT Pub. Date: Jun. 14, 2018

(65) Prior Publication Data
US 2019/0143053 A1    May 16, 2019

Related U.S. Application Data

(60) Provisional application No. 62/429,910, filed on Dec. 5, 2016.

(51) Int. Cl.
*A61M 15/00* (2006.01)
*B05B 17/00* (2006.01)
*A61M 11/00* (2006.01)

(52) U.S. Cl.
CPC ...... *A61M 15/0041* (2014.02); *A61M 11/005* (2013.01); *A61M 15/00* (2013.01);
(Continued)

(58) Field of Classification Search
CPC .. A61M 11/00; A61M 11/001; A61M 11/002; A61M 11/003; A61M 11/005;
(Continued)

(56) References Cited

U.S. PATENT DOCUMENTS 4,703,864 A * 11/1987 Larkin ................... B65D 41/48
215/256
4,969,883 A * 11/1990 Gilbert ................... A61J 1/2096
215/DIG. 3

(Continued)

FOREIGN PATENT DOCUMENTS

| CN | 202605462 U | 12/2012 |
|---|---|---|
| CN | 103563881 A | 2/2014 |

(Continued)

OTHER PUBLICATIONS

Cheng, Chunwang, The internationl search report and the written opinion of the Internaional Search Authority, dated Feb. 24, 2018, whole codument, SIPO as ISA.

*Primary Examiner* — Colin W Stuart
*Assistant Examiner* — Matthew D Ziegler
(74) *Attorney, Agent, or Firm* — Polsinelli PC; Emily C. Peyser

(57) ABSTRACT

An aerosol generating apparatus includes a vial, a cap assembly and a receptacle. The vial stores liquid medicament and includes a puncturable seal held in position by a retaining ring. The cap assembly includes an actuator with an interior bore extending therethrough, a perforated membrane coupled to the actuator, a fastener and a first mating element. The fastener is adapted to detachably secure the cap assembly to the vial such that the perforated membrane aligns with the puncturable seal. The receptacle receives the cap assembly with the vial. The receptacle includes a driving element and a second mating element capable of mating with the first mating element. The driving element aligns and (Continued)

communicates with the perforated membrane when the receptacle engages the cap assembly. The actuator pierces the puncturable seal to displace the liquid medicament through the interior bore to the perforated membrane and the driving element to generate aerosol.

19 Claims, 8 Drawing Sheets

(52) U.S. Cl.
CPC ...... *A61M 15/009* (2013.01); *A61M 15/0085* (2013.01); *B05B 17/0646* (2013.01); *A61M 15/0003* (2014.02); *A61M 15/0035* (2014.02); *A61M 2205/0294* (2013.01); *A61M 2209/045* (2013.01)

(58) Field of Classification Search
CPC .............. A61M 15/00; A61M 15/0001; A61M 15/0021; A61M 15/0028; A61M 15/003–0035; A61M 15/0041; A61M 15/0085; A61M 15/009; A61M 2205/0294; A61M 2210/06; A61M 2210/0625; B05B 17/0646
See application file for complete search history.

(56) References Cited

U.S. PATENT DOCUMENTS

| | | | | | |
|---|---|---|---|---|---|
| 5,167,816 | A | * | 12/1992 | Kruger | A61M 1/28 210/257.2 |
| 5,342,346 | A | * | 8/1994 | Honda | A61J 1/2089 604/411 |
| 5,411,499 | A | * | 5/1995 | Dudar | A61J 1/2089 604/411 |
| 5,429,614 | A | * | 7/1995 | Fowles | A61J 1/2089 604/201 |
| 5,766,147 | A | * | 6/1998 | Sancoff | A61J 1/2089 141/2 |
| 6,036,672 | A | * | 3/2000 | Allen | A61M 1/0064 604/167.02 |
| 6,161,536 | A | * | 12/2000 | Redmon | A61J 1/2093 128/200.14 |
| 6,364,865 | B1 | * | 4/2002 | Lavi | A61J 1/2089 604/411 |
| 6,382,442 | B1 | * | 5/2002 | Thibault | A61J 1/1406 215/247 |
| 6,537,263 | B1 | * | 3/2003 | Aneas | A61J 1/2089 604/412 |
| 7,628,779 | B2 | * | 12/2009 | Aneas | A61J 1/2096 604/411 |
| 8,075,545 | B2 | * | 12/2011 | Moy | A61J 1/1475 206/221 |
| 9,801,786 | B2 | * | 10/2017 | Lev | A61J 1/2096 |
| 9,956,138 | B2 | * | 5/2018 | Ohlin | B65D 51/002 |
| 2001/0030271 | A1 | * | 10/2001 | Weesner | A61M 5/008 248/316.7 |
| 2002/0020408 | A1 | * | 2/2002 | Knauer | A61M 15/0065 128/200.14 |
| 2003/0101995 | A1 | * | 6/2003 | Yamashita | A61K 9/0073 128/203.15 |
| 2007/0241136 | A1 | * | 10/2007 | Poulard | A61M 11/02 222/162 |
| 2009/0255532 | A1 | * | 10/2009 | Grunstad | A61M 16/183 128/202.27 |
| 2010/0101570 | A1 | * | 4/2010 | Meyer | A61M 15/0065 128/203.12 |
| 2011/0315786 | A1 | * | 12/2011 | Kambayashi | B05B 17/0646 239/102.2 |

FOREIGN PATENT DOCUMENTS

| | | | | |
|---|---|---|---|---|
| CN | 203609747 U | 5/2014 | | |
| CN | 2038427597 U | 9/2014 | | |
| CN | 104353164 A | 2/2015 | | |
| CN | 105396730 A | 3/2016 | | |
| WO | WO-2010017586 A1 | * | 2/2010 | .......... A61M 11/041 |
| WO | WO2016133856 A2 | 8/2016 | | |

* cited by examiner

AEROSOL GENERATING APPARATUS WITH REPLACEABLE PARTS

CROSS REFERENCE TO RELATED APPLICATION

The present application claims priority to PCT Application PCT/CN2017/114632 filed on Dec. 5, 2017, which claims priority to U.S. Provisional Application Ser. No. 62/429,910, filed on Dec. 5, 2016, the entire contents of which are hereby incorporated by reference into this application.

FIELD

The present disclosure relates to an aerosol generating apparatus and more particularly to an aerosol generating apparatus with replaceable vial assembly.

BACKGROUND

Nebulizer, also known as aerosolizer or atomizer, is used to deliver medication in fine particles/droplets to patients for inhalation. An aerosol generating module, which is a component of a nebulizer, receives liquid medicament to generate aerosol for treating a patient with respiratory conditions, such as Chronic Obstructive Pulmonary Disease (COPD). A typical aerosol generating module includes a perforated membrane and a vibratable element. One way for a vibratable element to generate vibration is through the incorporation of piezoelectric (PZT) materials. Vibration is provided to the liquid passing through the perforated membrane, thereby generating aerosol.

A reservoir or a liquid container such as a vial, with an internal chamber, stores the liquid medicament to be provided to the aerosol generating module. The vibratable element vibrates the perforated membrane, through which the liquid medicament permeates, to generate aerosol. Typically, the aerosol generating module is either permanently secured to the liquid container or integrally formed with the liquid container. The aerosol generating module may be permanently secured to the liquid container by adhesive or other known securing means. Accordingly, once the liquid medicament is depleted, the entire aerosol generating apparatus, including the aerosol generating module, is to be thrown away.

To achieve desired aerosolization, the liquid container may need to be cleaned prior to each use. The same applies to the perforated membrane. If the liquid container and/or the perforated membrane are not cleaned properly, the life of the nebulizer may be shortened. For example, residue may form and block either the perforated membrane or the opening of the liquid container. The foregoing may further lead to faster degradation of the vibratable element, thereby reduce the nebulization efficiency. Insufficient cleaning may also lead to contamination, which may jeopardize medical treatments. The abovementioned risks can be mitigated by using a new set of aerosol generating module and liquid container for every treatment. However, this will substantially increase the patient's financial burden. Therefore, the present disclosure aims to design an aerosol generating apparatus with replaceable components, such as a vial and the assembly thereof. Certain components may be disposed after each treatment, while others can be preserved for repeated use.

SUMMARY

The present disclosure provides an aerosol generating apparatus including a vial, a cap assembly and a receptacle. The vial is capable of storing liquid medicament and includes a puncturable seal held in position by a retaining ring. The cap assembly includes an actuator with an interior bore extending therethrough, a perforated membrane coupled to the actuator, a fastener, and a first mating element. The fastener is adapted to detachably secure the cap assembly to the vial such that the perforated membrane aligns with the puncturable seal. The receptacle is configured to receive the cap assembly with the vial, and the receptacle includes a driving element and a second mating element capable of mating with the first mating element of the cap assembly. The driving element aligns and communicates with the perforated membrane when the receptacle engages the cap assembly. Operation of the actuator pierces the puncturable seal, which allows the liquid medicament to be displaced through the interior bore to the perforated membrane. The driving element will vibrate the liquid medicament at the perforated membrane to generate aerosol.

The present disclosure also provides a replaceable vial assembly for an aerosol generator. The vial assembly includes a vial and a cap assembly. The vial is capable of storing liquid medicament. The vial includes a puncturable seal held in position by a retaining ring. The cap assembly includes a cap body and an actuator. The cap body includes a perforated membrane. The actuator is received within the cap body and includes an interior bore extending therethrough. The actuator couples to the perforated membrane such that the interior bore is in communication with the perforated membrane. The cap body is adapted for detachably snap engagement over the retaining ring such that the perforated membrane aligns with the puncturable seal. Upon movement of the actuator, the vial's puncturable seal is pierced and the liquid medicament flows from the vial through the interior bore to the perforated membrane. The replaceable vial assembly is adapted to detachably engage with an aerosol generator.

The present disclosure also provides a method for operating an aerosolizer. The liquid medicament is stored in a vial that includes a puncturable seal. A cap assembly is detachably secured over the vial to form a vial assembly. As a result, a perforated membrane on the cap assembly is aligned with the puncturable seal of the vial. The cap assembly, securing over the vial, is subsequently actuated to pierce the puncturable seal. The vial assembly is detachably engaged with a receptacle in a way that the liquid medicament is displaced to the perforated membrane by gravity. A driving element of the receptacle is aligned with the perforated membrane in a way that the driving element communicates with the perforated membrane. The driving element is activated to nebulize the liquid medicament passing through the perforated membrane for aerosol generation.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

Figure 1:
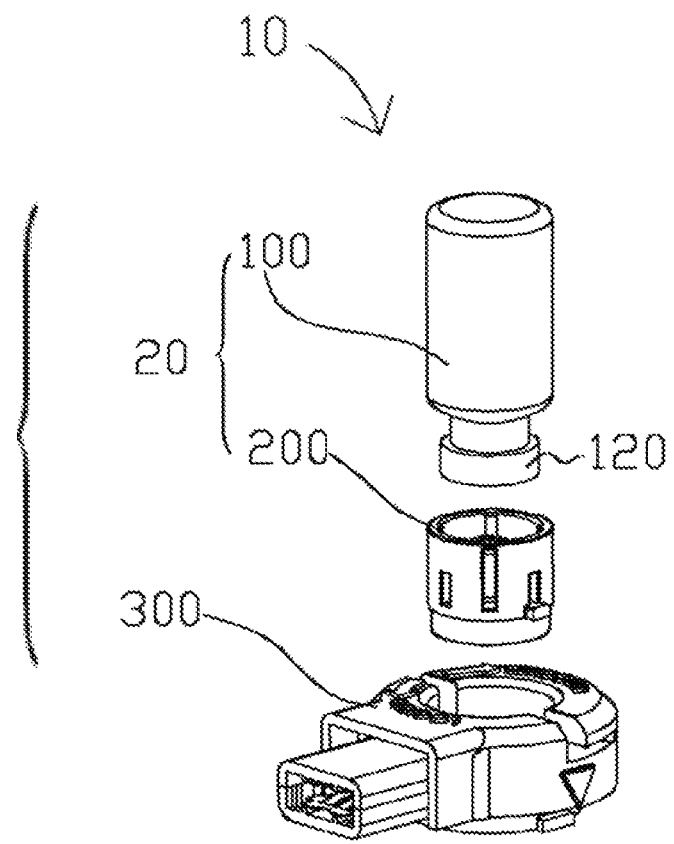
FIG. 1 illustrates an aerosol generating apparatus based on some embodiments of the present disclosure.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the disclosure. Any reference signs in the claims shall not be construed as limiting the scope. Like reference symbols in the various drawings indicate like elements.

DETAILED DESCRIPTION OF THE DISCLOSURE

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Throughout the various views and illustrative embodiments, like reference numerals are used to designate like elements. Reference will now be made in detail to exemplary embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, an apparatus in accordance with the present disclosure. It is to be understood that elements not specifically shown or described may take various forms. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. It should be appreciated that the following figures are not drawn to scale; rather, these figures are merely intended for illustration.

In the drawings, like reference numbers are used to designate like or similar elements throughout the various views, and illustrative embodiments of the present disclosure are shown and described. The figures are not necessarily drawn to scale, and in some instances the drawings have been exaggerated and/or simplified in places for illustrative purposes. One of ordinary skill in the art will appreciate the many possible applications and variations of the present disclosure based on the following illustrative embodiments of the present disclosure.

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise. Furthermore, relative terms, such as "bottom" and "top," may be used herein to describe one element's relationship to other elements as illustrated in the Figures.

It will be understood that elements described as "under" or "below" other elements would then be oriented "over" or "above" the other elements. The exemplary terms "under" or "below" can, therefore, encompass both an orientation of over and under.

Unless otherwise defined, all terms (including technical and scientific terms) used herein have the same meaning as commonly understood by one of ordinary skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

FIG. 1 illustrates an aerosol generating apparatus 10 based on some embodiments of the present disclosure. The aerosol generating apparatus 10 includes a vial assembly 20 and a receptacle 300. The vial assembly 20 includes a vial 100 and a cap assembly 200. The vial 100 contains liquid medicament. In one example, the vial 100 is designed for a single dosage. As will be discussed in subsequent disclosures and embodiments, the cap assembly 200 is detachably securable to the vial 100. When the cap assembly 200 is secured to the vial 100, the vial assembly 20 is formed. The vial assembly 20 is designed in a way that it can detachably engage the receptacle 300, i.e., it is removable. When engaged with the receptacle 300, the liquid medicament is directed to flow through the cap assembly 200 and release to the receptacle 300 for nebulization. The vial assembly 20 is removable and disposable, whereas the receptacle 300 is designed for repeated use. In this way, the cost of using the aerosol generating apparatus 10 is substantially reduced. The disposable nature of the vial assembly 20 also reduces the risk of contamination, because a new set of vial assembly 20 and the medication therein is used in every new treatment cycle. Users may always inhale fresh and precise amount of medication in each treatment. Moreover, when the vial assembly 20 is disengaged, a user may further clean and sterilize the rest of the aerosol generating apparatus 10. The foregoing decreases the chances of clogging of the aerosol generating apparatus 10, thus increasing its life and the aerosolization efficiency.

Figure 2:
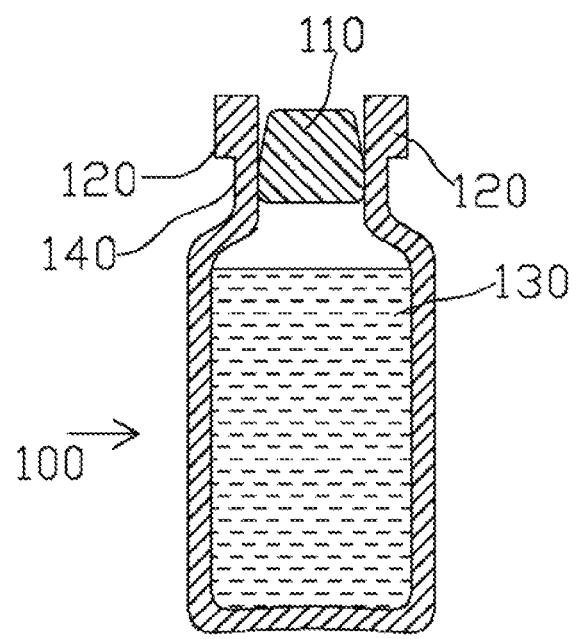
FIG. 2 illustrates a lateral view of a vial according to some embodiments of the present disclosure.

FIG. 2 illustrates a lateral view of the vial 100 according to some embodiments of the present disclosure. The vial 100 includes a puncturable seal 110 and a retaining ring 120. The puncturable seal 110 can be a metal or inert plastic layer or an elastomer stopper or any conventional means that can securely close a vial. The puncturable seal 110 is held in sealing engagement to a neck 140 of the vial 100 by means of the retaining ring 120 provided with a central aperture which allows the insertion of an actuator to break the seal, i.e., either by pushing the stopper into the vial 100 or by puncturing the sealing layer. The retaining ring 120 may be made of metal such as anodized aluminum. The vial 100 also stores a liquid medicament 130. The amount of the liquid medicament 130 can be adjusted, depending on the dosages desired, e.g. single or multiple. In another embodiment, the puncturable seal 110 is covered to the top surface of the retaining ring 120. The puncturable seal 110 prevents the liquid medicament 130 from leaking out of the vial 100 and ensures that there is no fluid or air communication with the exterior environment.

Figure 3:
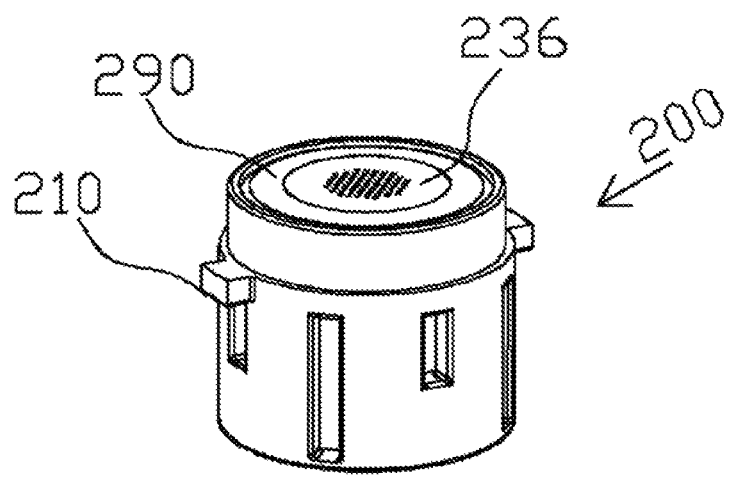
FIGS. 3-4 illustrate a top view and a perspective view of a cap assembly according to some embodiments of the present disclosure.
Figure 4:
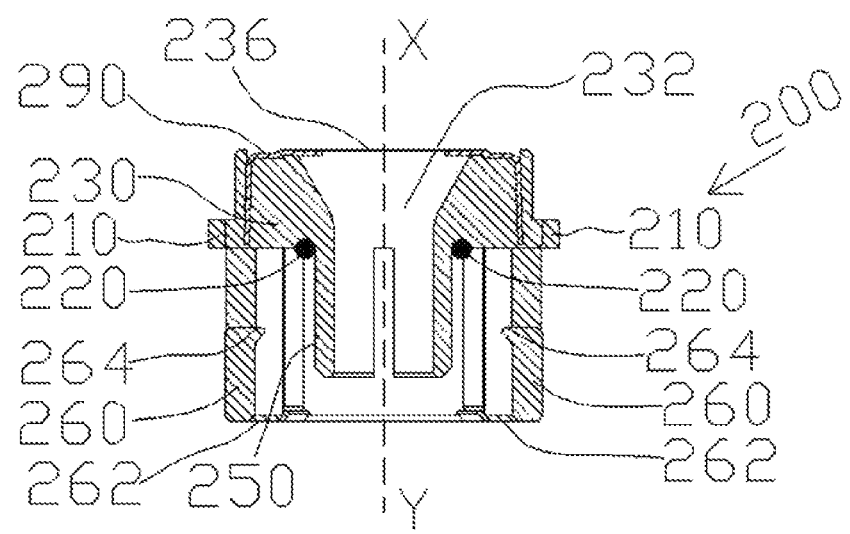
Figure 5:
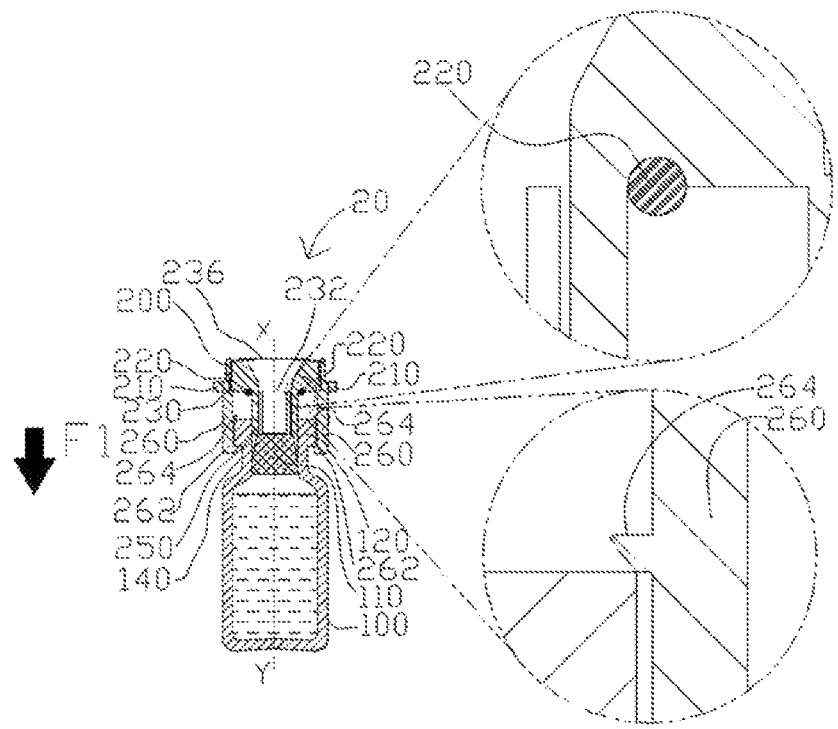
FIGS. 5-7 illustrate a process of securing the cap assembly to the vial to get the liquid medicament ready for nebulization, based on some embodiments of the present disclosure.
Figure 6:
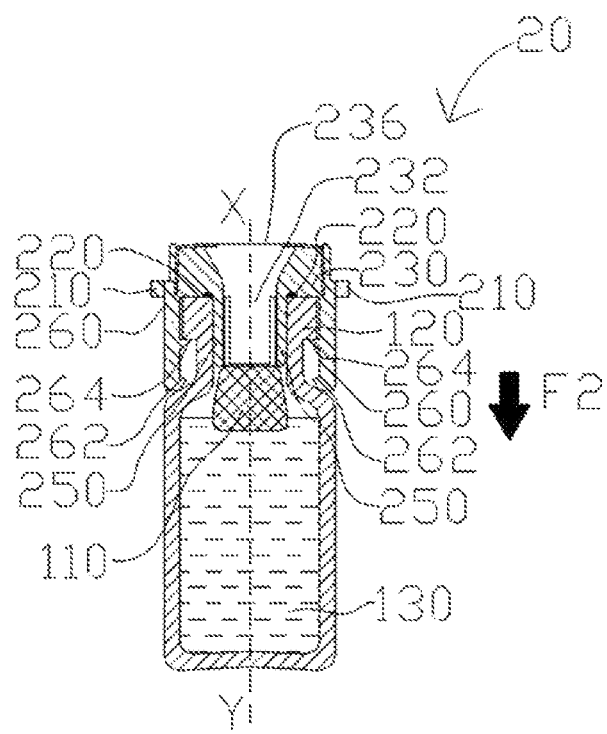
Figure 7:
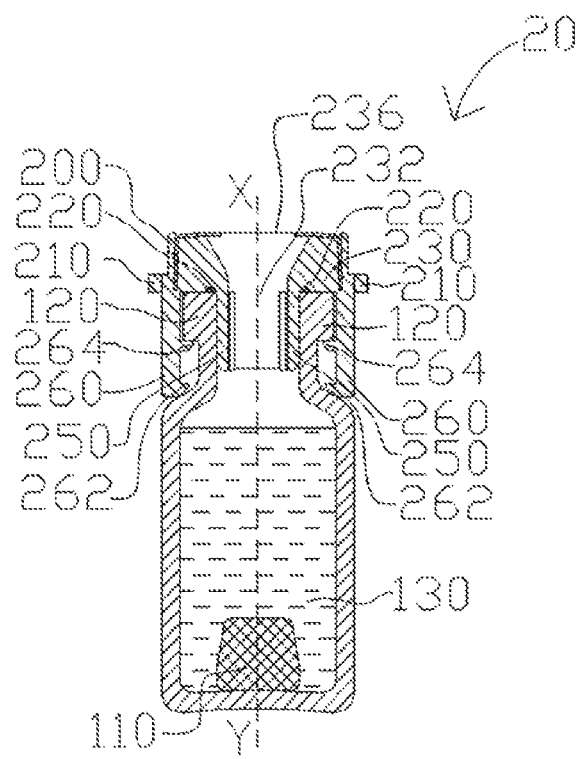
Figure 8:
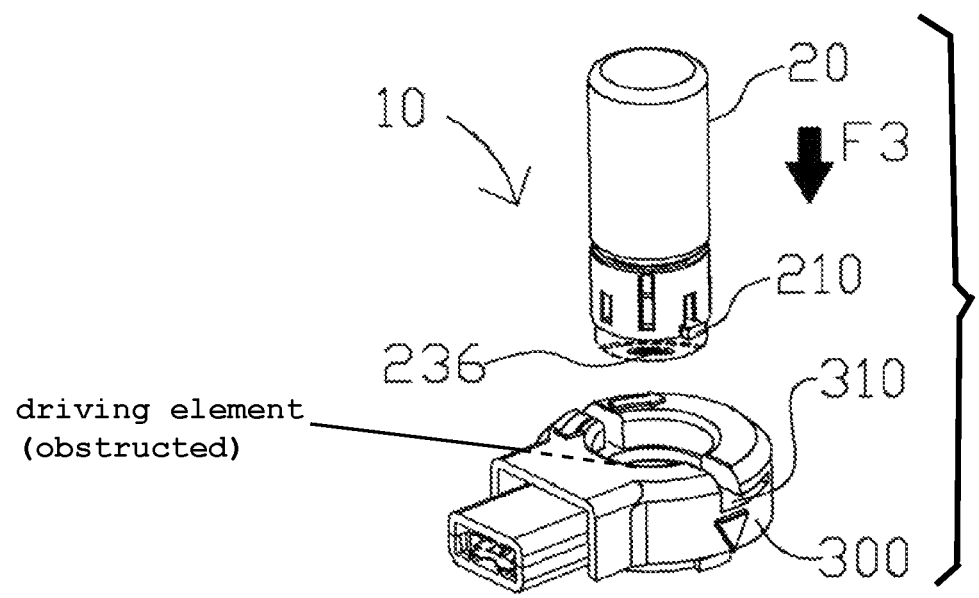
FIGS. 8-11 illustrate the application method of the aerosol generating apparatus based on some embodiments of the present disclosure.
Figure 9:
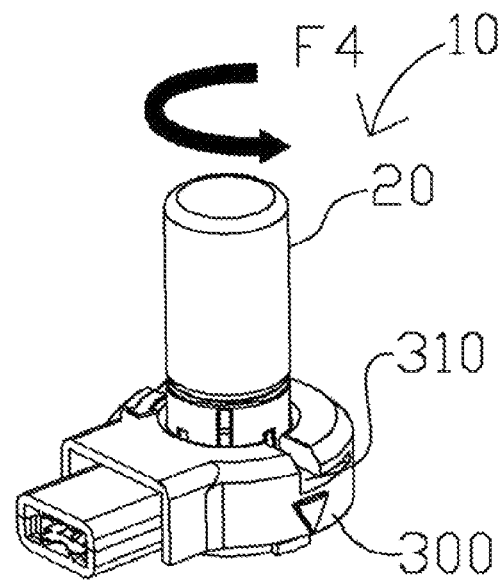

FIGS. 3-4 illustrate a top view and a perspective view of the cap assembly 200 of the aerosol generating apparatus 10 according to some embodiments of the present disclosure. The cap assembly 200 includes a circumferentially extending rib 210, an actuator 230, a perforated membrane 236, a fastener 260 and a cap body 290. The cap assembly 200 can detachably engage with a receptacle 300 via the rib 210. In one example, the fastener 260 is equipped on the cap body 290. The perforated membrane 236 is made of a macromolecular polymer of polyimide, polyethylene (PE), polypropylene (PP), polyether ether ketone (PEEK) and/or the combination thereof. In some embodiments, the perforated membrane 236 may be integrally formed with the cap body 290; the two are made of the same material or same combination of materials. In some embodiments, the cap body 290 is made of metal. The perforated membrane 236 is affixed to the top surface of the cap body 290. The actuator 230 includes an interior bore 232 extending therethrough, providing a passage through which the liquid medicament 130 can travel from the vial 100 to the perforated membrane 236. Particularly, the actuator 230 is coupled to the perforated membrane 236 such that the interior bore 232 communicates with the perforated membrane 236. The actuator 230 is also received within the cap body 290. Specifically, the actuator 230, along with the cap body 290, is adapted to move along the X-Y direction (as shown in FIGS. 4-7) upon operation in order to break or move the puncturable seal 110. When the cap assembly 200 is secured to the vial 100, the fastener 260 secures the cap assembly 200 to the retaining ring 120 at the neck 140 of the vial 100, in a detachable manner, and aligns the perforated membrane 236 with the puncturable seal 110.

The fastener 260 may detachably secure the cap assembly 200 to the vial 100 using different coupling mechanisms. The coupling mechanisms include snap fit, interference fit, tongue-and-groove fit, post-and-bore fit, and press fit. In a preferred embodiment, the fastener 260 may be configured for detachably snap engagement of the cap assembly 200 over the retaining ring 120 at the neck 140 of the vial 100. The engagement is adapted to align the perforated membrane 236 with the vial's seal 110. It is to be noted that the present disclosure is not so limited, and a person having ordinary skill understands that any coupling mechanisms known in the art are within the scope of the present disclosure.

In certain embodiments, the actuator 230 includes one or multiple projection(s) 250 that extends from the interior bore 232. Foolproof designs may be provided to the actuator 230 to prevent the puncturable seal 110 from blocking the flow of the liquid medicament 130 when the vial 100 is inverted. For example, projections 250 may be arranged to be circumferentially spaced such that liquid medicament 130 may flow into the interior bore 232 through the spaces between the projections 250. In other embodiments, lengths of the projections 250 extending from the interior bore 232 may not be equal. Accordingly, the liquid medicament 130 may flow through the space formed by unequal lengths of the projections 250. In certain embodiments, the projection 250 is a ring-shaped projection, a sidewall of which has at least one through hole. In this way, the liquid medicament may flow to the interior bore 232 through the through hole even if an opening formed on the ring-shaped projection is obstructed by the puncturable seal 110.

In certain embodiments, the cap assembly 200 may also include an O-shaped ring 220 sandwiched between the actuator 230 and the retaining ring 120. When the cap assembly 200 is secured to the vial 100, the O-shaped ring 220 provides liquid or air tight seal by filling the tiny gap (not shown) between the actuator 230 and the retaining ring 120. In this way, when the puncturable seal 110 is pierced and the vial 100 is inverted, the seal provided by the O-shaped ring 220 prevents any leakage of the liquid medicament 130. In other words, the O-shaped ring 220 ensures that the liquid medicament 130 only exits the vial 100 through the interior bore 232 to the perforated membrane 236.

FIGS. 5-7 illustrate a process of securing the cap assembly 200 to the vial 100 based on some embodiments of the present disclosure. The vial assembly 20 is formed once the cap assembly 200 is secured to the vial 100, and the liquid medicament 130 may communicate with the perforated membrane 236 for nebulization. FIG. 5 illustrates a first position of the actuator 230. FIG. 6 illustrates a second position of the actuator 230. FIG. 7 illustrates an exemplary state when the puncturable seal 110 is pierced.

In certain embodiments, the process of securing the cap assembly 200 to the vial 100 is split into two phases.

In the first phase as illustrated in FIG. 5, the actuator 230 is at the first position when an aligning force F1 moves the cap assembly 200 towards the vial 100, permitting the fastener 260 to secure the cap assembly 200 to the vial, i.e., by clamping to the neck 140 of the vial 100. In another example, the fastener 260 may be configured to be abutments 262 and 264 that can detachably snap engage the vial 100. In one example, the abutments 262 and 264 are circumferentially spaced and inwardly projecting. In this first phase, the puncturable seal 110 has not been pierced while the actuator 230 may or may not touch the puncturable seal 110.

In the second phase as illustrated in FIG. 6, the actuator 230 is moved to the second position by an actuating force F2. That is, upon actuation, the actuator 230 moves to the second position to puncture the puncturable seal 110. In certain embodiments, the puncturable seal 110, which may be an elastomer stopper, will be pushed into the vial 100 by the actuator 230 in the second phase. In certain embodiments, the actuating force F2 is larger than the aligning force F1 because puncturing the puncturable seal 110 requires a larger force than that of merely moving the cap assembly 200 towards the vial 100. As further illustrated in FIG. 7, the elastomer stopper drops into the vial 100 after being pushed in by the actuator 230. In some other embodiments, the puncturable seal 110, which may be a metal or plastic layer, is pierced by the actuator 230 in this second phase.

Under certain circumstances, a user of the aerosol generating apparatus 10 may prefer the vial 100 and the cap assembly 200 to be pre-assembled. In the first phase, the user may carry the vial 100 and the cap assembly 200 together while keeping the puncturable seal 110 intact. Such design prevents the hassle of carrying two separate components FIGS. 8-11 illustrate how to assemble the aerosol generating apparatus 10. Particularly, the vial assembly 20 is adapted to detachably engage the receptacle 300, e.g. in a removably seatable manner, such that the vial assembly 20 is removable and can be replaced when needed. In FIG. 8, the vial assembly 20 is inverted in order to engage the receptacle 300. Particularly, the inverted vial assembly 200 ensures that the liquid medicament 130 may reach the perforated membrane 236 by gravity when the puncturable seal 110 is removed. A force F3 is applied to engage the vial assembly 200 with the receptacle 300. Specifically, in one example, the rib 210 on the cap assembly 200 mates with a mating groove 310 on the receptacle 300 in a removably seatable manner. In some examples, the rib 210 may be a first mating element of any available form, and the mating groove 310 may be a second mating element of any available form, as long as the first and second mating element can properly engage each other. In some examples, the mating mechanism between the first mating element and the second mating element may be one of a snap fit, an interference fit, a tongue-and-groove fit, a post-and-bore-fit, and a press fit. In FIG. 9, the vial assembly 20 is further rotated to slide the rib (not shown) further into the mating groove 310 via a rotational force F4. As a result, the vial assembly 20 is securely engaged to the receptacle 300. Consequently, a driving element of the receptacle 300 (not shown) is aligned and in contact with the perforated membrane (not shown). Particularly, the driving element includes a piezoelectric element coupled to a substrate that may be made of metal. The substrate includes a projection in contact with the perforated membrane, and vibration energy generated by the piezoelectric element is transmitted to the perforated membrane via the projection for nebulization. In certain embodiments, the projection may deform, i.e., press against, the perforated membrane to an extent in order to achieve better nebulization effects. The liquid medicament 130 may flow out of the vial 100, through the internal bore 232 of the actuator 230 (not shown) to the perforated membrane 236 (not shown), at which aerosolization occurs when the driving element vibrates the liquid medicament 130.

Figure 10:
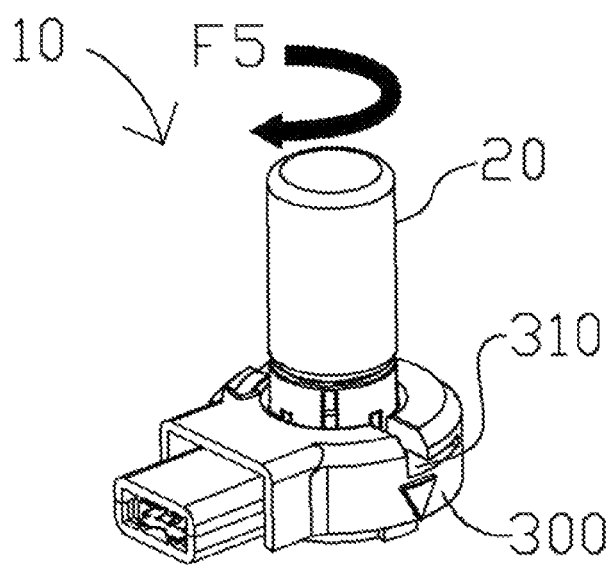
Figure 11:
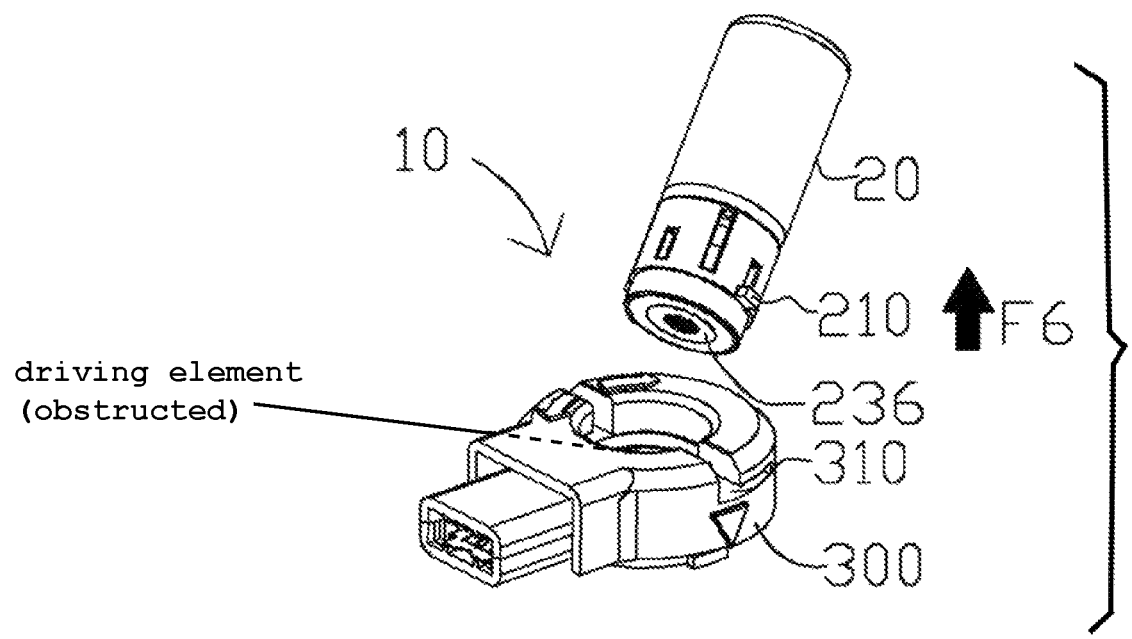

In FIG. 10, when the liquid medicament 130 is depleted and/or a user intends to replace the vial assembly 20, the vial assembly 20 can be disengaged by rotating it in a direction opposite to that of engagement via a rotational force F5. In other words, the rib 210 slides away from a secured position to permit the vial assembly 20 to be disengaged. In FIG. 11, the vial assembly 20 is removed from the receptacle 300 via a disengaging force F6. The vial assembly 20 may be disposed.

Figure 12:
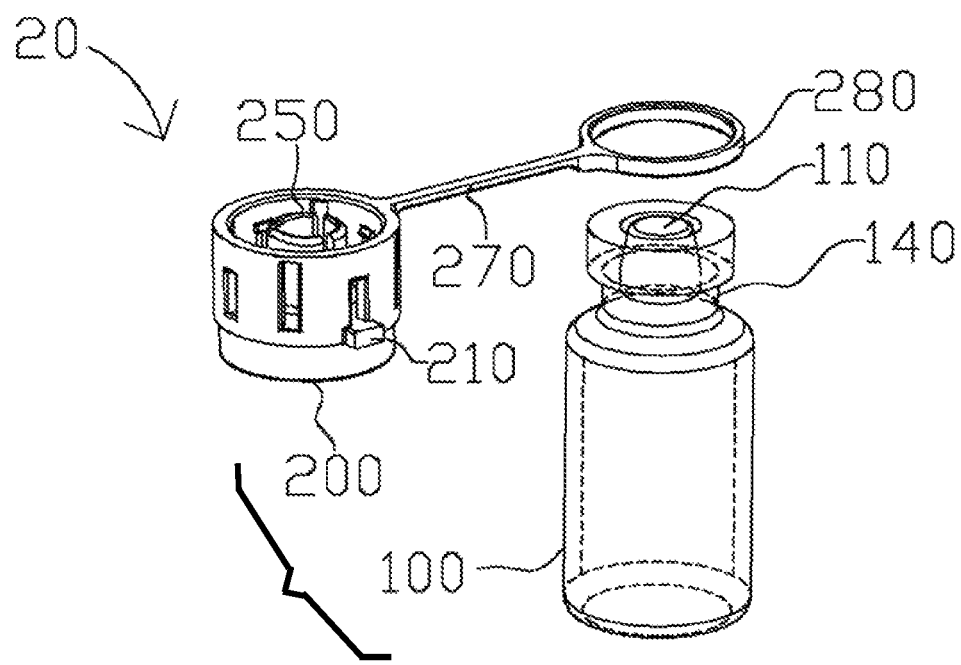
FIGS. 12-14 illustrate a design of the cap assembly based on some embodiments of the present disclosure.
Figure 13:
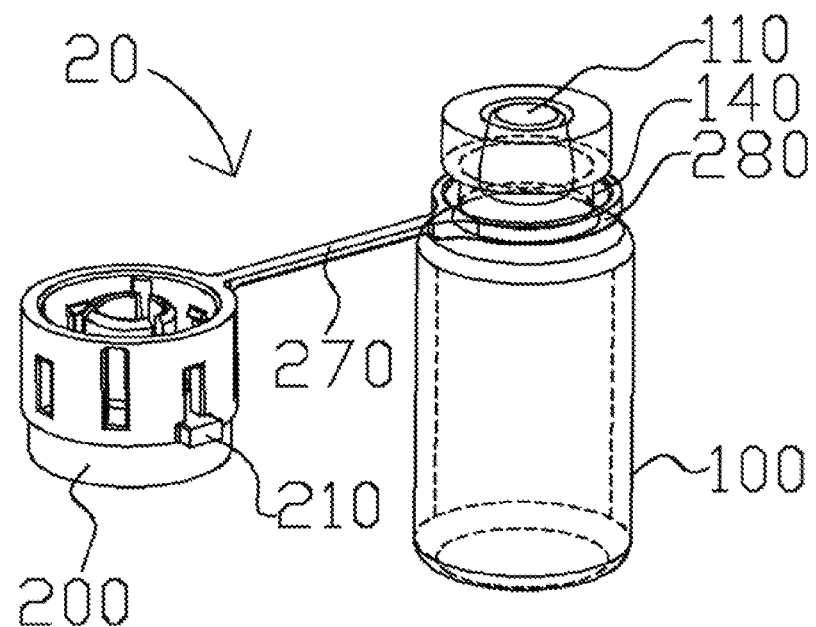
Figure 14:
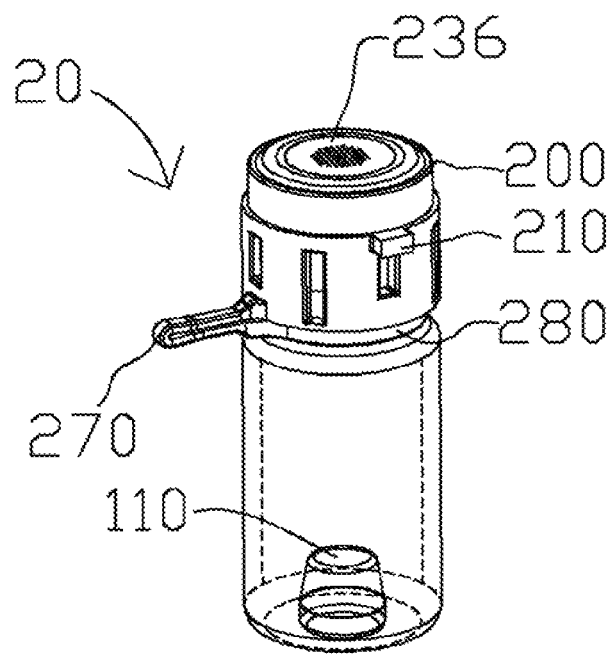

FIGS. 12-14 illustrate the designs of the cap assembly 200 based on some embodiments of the present disclosure. The cap assembly 200 may further include a flexible arm 270 and a collar 280 coupled to the flexible arm 270. The collar 280 engages the vial 100 at the neck 140, as illustrated in FIG. 13. The flexible arm 270 prevents the cap assembly 200 from being separated from the vial 100 when the cap assembly 200 is not engaged with the vial 100. With the aid of the aforementioned components, the cap assembly 200 can be pre-coupled to the vial 100. When the vial assembly 20 is to be used for nebulization, the flexible arm 270 may be bent to allow the cap assembly 200 to engage the vial 100. As illustrated in FIG. 14, the engagement of the cap assembly 200 with the vial 100 punctures the seal by pushing the puncturable seal (e.g. a stopper) 110 into the vial 100.

Figure 15:
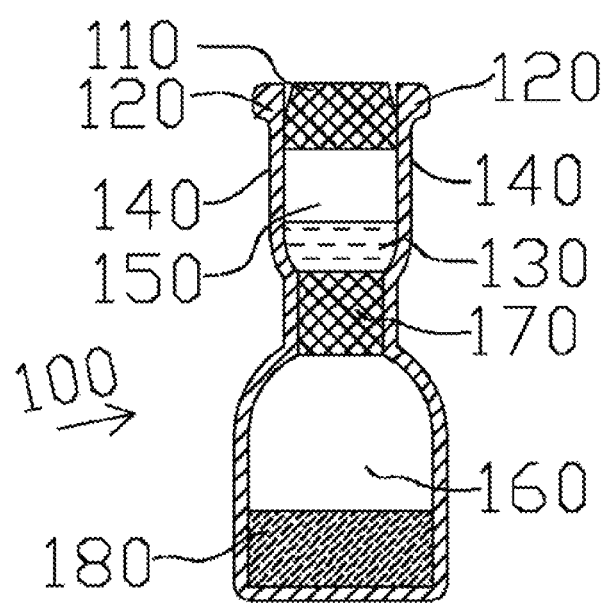
FIG. 15 illustrates a design of the vial based on some embodiments of the present disclosure.

FIG. 15 illustrates a design of the vial 100 based on some embodiments of the present disclosure. The vial 100 may include a first chamber 150 and a second chamber 160. The first chamber 150 is closer to the opening of the vial 100 than the second chamber 160. The first chamber 150 is separated from the second chamber 160 by a seal 170 that is liquid tight to or air tight. In certain embodiments, the seal 170 is a diaphragm. In one example, the first chamber 150 is used for storing the liquid medicament 130, and the second chamber 150 is used for depositing a solid medicament 180, e.g. in forms of powder. When the puncturable seal 110 is punctured by engagement of the cap assembly 200 to the vial 100, the hydraulic pressure of the first chamber 150 is increased. In this way, the seal 170 is also punctured by the first chamber 150's increasing pressure. Accordingly, the two chambers 150 and 160 become communicative such that the liquid medicament 130 and the solid medicament 180 can be mixed. The solid medicament 180 can be better preserved with such design. In one example, the first chamber 150 may be a vacuum, and the liquid medicament is disposed in the second chamber 160. Accordingly, even if the seal 110 is compromised and the first chamber 150 is exposed to exterior environment, the seal to the liquid medicament is still intact. In other words, the foregoing setting provides additional security, preventing the liquid medicament from becoming in contact with the environment before desired use.

Operation or movement of the actuator in the present disclosure is not to be limited to a specific manner. In one example, actuation may occur when a user pushes the cap assembly 200, which includes the actuator 230 therein, against the vial 100 in order to allow the actuator to break or move the puncturable seal 110. Another example of actuation may be in the form of screwing the cap assembly 200 on the vial 100 with continuous threads until the puncturable seal 110 is pierced.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An aerosol generating apparatus, comprising:
a vial for storing liquid medicament comprising a penetrable seal;
a cap assembly comprising an actuator with an interior bore extending therethrough, the interior bore having a first end and a second end and open fluid communication between the first end and the second end, a perforated membrane coupled to the cap assembly and disposed at or near the first end of the interior bore of the actuator, a fastener and a first attachment element, wherein the fastener is adapted to detachably secure the cap assembly to the vial in a first position such that the penetrable seal aligns with the second end of the interior bore of the actuator; and
a receptacle for receiving the cap assembly with the vial, the receptacle including a driving element which is coupled to a substrate and a second attachment element configured to attach with the first attachment element of the cap assembly, wherein the perforated membrane projects over and communicates with the driving element when the receptacle engages the cap assembly, and the perforated membrane, wherein the actuator, when actuated from the first position to a second position, is configured to penetrate the penetrable seal such that the liquid medicament is displaced through the interior bore from the second end to the perforated membrane at or near the first end and the driving element is configured to vibrate the liquid medicament at the perforated membrane via the substrate to generate aerosol through the receptacle; and wherein the actuator is in a first position when the fastener detachably secures the cap assembly to the vial and the actuator is configured to move to a second position to penetrate the penetrable seal.

2. The aerosol generating apparatus of claim 1, wherein the fastener includes a coupling mechanism selected from the group consisting of a snap fit, and interference fit, a tongue and groove fit, a post-and-bore-fit, and a press fit.

3. The aerosol generating apparatus of claim 1, wherein the actuator comprises at least one projection that extends from the interior bore and is adapted to penetrate the penetrable seal.

4. The aerosol generating apparatus of claim 3, wherein at least one projection extends around the circumference of the interior bore of the actuator, and the liquid medicament flows to the interior bore through a space between the at least one projection.

5. The aerosol generating apparatus of claim 1, wherein aerosolization is configured to occur at the perforated membrane when the driving element vibrates the liquid medicament that flowed through the interior bore.

6. The aerosol generating apparatus of claim 1, wherein the cap assembly further comprises a flexible arm and a collar coupled to the flexible arm, wherein the collar mates with a neck of the vial, and the flexible arm is adapted to prevent the cap assembly from being separated from the vial when the cap assembly is not engaged with the vial.

7. The aerosol generating apparatus of claim 1, wherein the vial further comprises a first chamber and a second chamber, the first chamber is closer to an opening of the vial than the second chamber, and the second chamber is separated from the first chamber using a divider that is diffusion-tight to air or liquid.

8. The aerosol generating apparatus of claim 7, wherein the divider is a diaphragm.

9. The aerosol generating apparatus of claim 1, wherein the vial is configured to detachably engage the receptacle.

10. The aerosol generating apparatus of claim 1, wherein the first attachment element includes a circumferentially extending rib and the second attachment element includes a groove, wherein the circumferentially extending rib is removably attachable in the attachment groove.

11. The aerosol generating apparatus of claim 1, wherein the cap assembly further comprises an O-shaped ring to provide a liquid or air tight seal between the actuator and the vial.

12. The aerosol generating apparatus of claim 11, where the O-shaped ring is sandwiched between the actuator and the vial.

13. The aerosol generating apparatus of claim 1, wherein the vial is further adapted to store the liquid medicament as a single dosage.

14. The aerosol generating apparatus of claim 1, wherein the driving element includes a piezoelectric element coupled to a substrate.

15. The aerosol generating apparatus of claim 1, wherein the vial includes a retainer ring surrounding the penetrable seal.

16. The aerosol generating apparatus of claim 1, wherein the perforated membrane is fixed to the cap assembly.

17. A replaceable vial assembly for an aerosol generator comprising:
a vial for storing liquid medicament comprising a penetrable seal; and
a cap assembly comprising:
a cap body including a perforated membrane; and
an actuator received within the cap body and includes an interior bore extending there through, the interior bore having a first end and a second end and open fluid communication between the first end and the second end, wherein the actuator couples to the cap body such that the interior bore is in communication with the perforated membrane;
wherein the cap body defines a fastener for detachable engagement with the vial in a first position such that the perforated membrane aligns with the penetrable seal;
wherein upon movement of the actuator from the first position to a second position, the penetrable seal of the vial is penetrated and the liquid medicament flows from the vial through the interior bore to the perforated membrane; and wherein the actuator is in a first position when the fastener detachably secures the cap assembly to the vial and the actuator is configured to move to a second position to penetrate the penetrable seal.

18. A method for operating an aerosolizer, comprising:
storing liquid medicament in a vial comprising a penetrable seal;
detachably securing a cap assembly over the vial in a first position to form a vial assembly, such that a perforated membrane coupled to the cap assembly aligns with the penetrable seal;
actuating the cap assembly from the first position to a second position to penetrate the penetrable seal;
detachably engaging the vial assembly to a receptacle such that the liquid medicament is configured to be displaced through an interior bore of the cap assembly from the vial to the perforated membrane by gravity;
aligning a driving element coupled to the receptacle with the perforated membrane such that the perforated membrane projects over the driving element and the driving element communicates with the perforated membrane; and
activating the driving element to nebulize the liquid medicament for generating aerosol.

19. The method of claim 18, wherein an aligning force for moving the cap assembly towards the vial when an actuator at the cap assembly is moved to a first position, and wherein an actuating force is used for puncturing the penetrable seal when the actuator is moved from the first position to a second position, and wherein the actuating force is larger than the aligning force.

* * * * *